ns Patent [19]

United States Patent [19]

Schromm et al.

[11] 4,015,011
[45] Mar. 29, 1977

[54] PHENYLALKYLAMINES AND SALTS THEREOF

[75] Inventors: Kurt Schromm; Anton Mentrup; Ernst Otto Renth, all of Ingelheim Am Rhein, Germany; Ludwig Pichler, Vienna, Austria; Werner Traunecker, Ingelheim Am Rhein, Germany

[73] Assignee: Boehringer Ingelheim GmbH, Ingelheim am Rhein, Germany

[22] Filed: Apr. 25, 1975

[21] Appl. No.: 571,719

[30] Foreign Application Priority Data

Apr. 27, 1974 Germany .......................... 2420618

[52] U.S. Cl. ........................ 424/324; 260/553 A; 260/570.8 R; 260/562 R; 260/465 E; 424/322; 424/330; 424/304
[51] Int. Cl.² ..................................... A61K 31/165
[58] Field of Search ................ 424/324; 260/562 R

[56] References Cited
UNITED STATES PATENTS 3,407,056  10/1968  Schwartz ............................ 71/118

Primary Examiner—Leonard Schenkman
Attorney, Agent, or Firm—Hammond & Littell

[57] ABSTRACT

Compounds of the formula

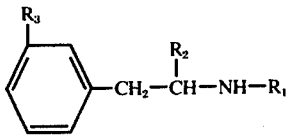

wherein
  $R_1$ is hydrogen, $-(CH_2)_n-R_4$ or $-CO-R_5$, where $n$ is 1 or 2,
  $R_4$ is hydrogen, cyano or benzoyl, and
  $R_5$ is hydrogen, lower alkoxy, benzyloxy, $-CH_2-NH_2$, $-CH(CH_3)-NH_2$, $-CH_2-NH-CH_2-C_6H_5$ or $-CH(CH_3)-NH-CH_2-C_6H_5$,
  $R_2$ is hydrogen or methyl, and
  $R_3$ is amino, nitro, $-NH-CO-R_6$ or $-NH-A-R_7$, where
  $R_6$ is hydrogen, methyl, methoxy, ethoxy, methylthio or ethylthio,
  $R_7$ is amino, methylamino or dimethylamino, and
  A is $-CO-$ or $-SO_2-$, and non-toxic, pharmacologically acceptable acid addition salts thereof; the compounds as well as their salts are useful as hypertensives.

5 Claims, No Drawings

PHENYLALKYLAMINES AND SALTS THEREOF

This invention relates to novel phenylalkylamines and non-toxic acid addition salts thereof, as well as to various methods of preparing these compounds.

More particularly, the present invention relates to a novel class of racemic or optionally active 1-phenyl-2-amino-ethanes or -propanes represented by the formula

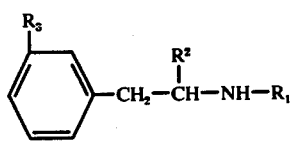

(I)

wherein
$R_1$ is hydrogen, $-(CH_2)_n-R_4$ or $-CO-R_5$, where $n$ is 1 or 2,
$R_4$ is hydrogen, cyano or benzoyl, and
$R_5$ is hydrogen, lower alkoxy, benzyloxy, $-CH_2-NH_2$, $-CH(CH_3)-NH_2$, $-CH_2-NH-CH_2-C_6H_5$ or $-CH(CH_3)-NH-CH_2-C_6H_5$,
$R_2$ is hydrogen or methyl, and
$R_3$ is amino, nitro, $-NH-CO-R_6$ or $-NH-A-R_7$, where
$R_6$ is hydrogen, methyl, methoxy, ethoxy, methylthio or ethylthio,
$R_7$ is amino, methylamino or dimethylamino, and
A is $-CO-$ or $-SO_2-$,
and non-toxic, pharmacologically acceptable acid addition salts thereof.

A preferred subgenus thereunder is constituted by those compounds of the formula I wherein $R_1$ is hydrogen, formyl, aminoacetyl or aminopropionyl, $R_2$ has the meanings defined above, and $R_3$ is amino, formylamino, methoxycarbonylamino or ureido, and their non-toxic, pharmacologically acceptable acid addition salts.

An especially preferred subgenus thereunder is constituted by those compounds for the formula I wherein $R_1$ is hydrogen, formyl, aminoacetyl or aminopropionyl, $R_2$ is methyl, and $R_3$ is formylamino, and their non-toxic, pharmacologically acceptable acid addition salts.

The compounds embraced by formula I may be prepared by the following methods:

Method A

For the preparation of a compound of the formula I wherein $R_3$ is $-NH-CO-R_6$ or $-NH-A-R_7$, by reacting a 1-(m-amino-phenyl)-2-amino-alkane of the formula

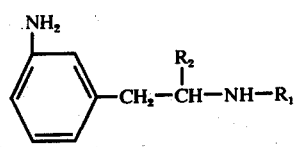

(II)

wherein $R_1$ and $R_2$ have the same meanings as in formula I, with a compound of the formula

  (III)

or

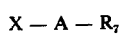  (IIIa)

wherein
$R_6$, $R_7$ and A have the same meanings as in formula I, and
X is halogen, especially chlorine or bromine, or, when $R_6$ is hydrogen or methyl, also $-O$-acyl or $-OH-$.

If necessary, the amino group or groups in the $-NH-R_1$ moiety of compound II may be protected by salt formation during the reaction.

A starting compound of the formula II may be prepared, for example, by reducing a corresponding 3-nitro-substituted compound.

Method B

For the preparation of a compound of the formula I wherein $R_1$ is hydrogen, methyl or ethyl, and $R_3$ is amino, $-NH-CO-R_6$ or $-NH-A-R_7$, where $R_6$, $R_7$ and A have the meanings previously defined, by reducing a compound of the formula

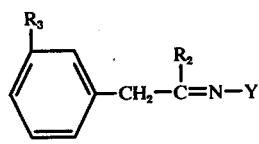

(IV)

wherein
$R_2$ and $R_3$ have the same meanings as in formula I, and
Y is hydrogen, methyl, ethyl, hydroxyl, amino or ureido,
with hydrogen in the presence of a hydrogenation catalyst, such as Raney nickel, platinum or palladium, or with a complex hydride, such as sodium borohydride.

A starting compound of the formula IV wherein Y is hydrogen, methyl or ethyl, i.e. a Schiff's base, may be prepared in situ in conventional manner from a ketone or the formula

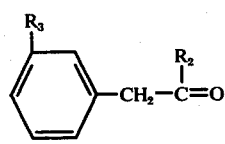

(V)

wherein $R_2$ and $R_3$ have the same meanings as in formula I.

A starting compound of the formula IV wherein Y is hydroxyl, amino or ureido may be obtained by reacting a ketone of the formula V with hydroxylamine, hydrazine or semicarbazide.

A starting compound of the formula IV wherein Y is hydroxyl may also be obtained by catalytic hydrogenation of a nitro-olefin of the formula

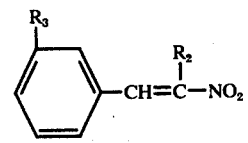

(VI)

wherein $R_2$ and $R_3$ have the same meanings as in formula I, in pyridine in the presence of palladized charcoal as a catalyst.

A compound of the formula V wherein $R_3$ is —NH—CO—$R_6$ or —NH—A—$R_7$, where $R_6$, A and $R_7$ have the meanings previously defined, may be obtained from an aniline of the formula

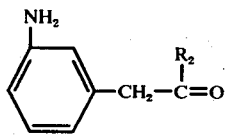 (VII)

wherein $R_2$ has the same meanings as in formula I, by the procedure described under method A.

Method C

For the preparation of a compound of the formula I wherein $R_1$ is hydrogen, methyl or ethyl, and $R_3$ is amino, —NH—CO—$R_6$ or —NH—A—$R_7$, where $R_6$, A and $R_7$ have the meanings previously defined, by catalytic hydrogenation or a compound of the formula

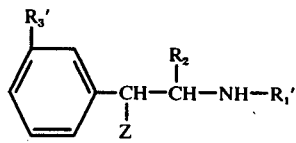 (VIII)

wherein
$R_1'$ is hydrogen, methyl or ethyl,
$R_2$ has the same meanings as in formula I,
$R_3'$ is amino, —NH—CO—$R_6$ or —NH—A—$R_7$, where $R_6$, $R_7$ and A have the meanings previously defined, and
Z is halogen, especially chlorine,
in the presence of a conventional hydrogenation catalyst, such as Raney nickel, platinum or palladium.

A starting compound of the formula VIII may be obtained by reacting an alcohol of the formula

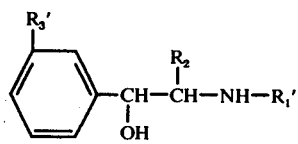 (IX)

wherein
$R_1'$ and $R_3'$ have the same meanings as in formula VIII, and
$R_2$ has the same meanings as in formula I,
with a halogenating agent, such as thionyl chloride or phosphorus pentachloride, An alcohol of the formula IX may be obtained from known compounds by conventional methods.

Method D

For the preparation of a compound of the formula I wherein $R_1$ has the meanings previously defined except hydrogen, an $R_3$ has the meanings previously defined except nitro, by N-alkylation of a compound of the formula

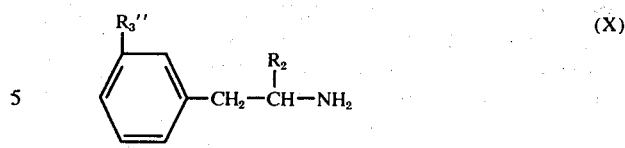 (X)

wherein
$R_2$ has the same meanings as in formula I, and
$R_3''$ has the meanings of $R_3$ in formula I except amino, with a compound of the formula $$X' - R_1'' \qquad (XI)$$

wherein
X' is a radical which is easily split off and combines with one hydrogen of the amino group of compound X to form a compound HX', preferably halogen and especially chlorine or bromine, and
$R_1''$ has the meanings of $R_1$ in formula I except hydrogen.

When $R_1''$ is —$(CH_2)_n$—$R_4$, where n and $R_4$ have the meanings previously defined, X' may also be a sulfonic acid radical, and when $R_1''$ is —CHO, X' may also be O-acyl, preferably $CH_3COO$—, or hydroxyl.

Prior to the N-alkylation, the compound of the formula X is advantageously first converted into a Schiff's base, for instance with benzaldehyde, and the imonium salt formed by the action of the N-alkylating agent upon the Schiff's base is subsequently cleaved under alkaline conditions.

A starting compound of the formula X may be obtained by conventional methods, for instance by catalytic hydrogenation of a compound of the formula V in the presence of ammonia.

Method E

For the preparation of a compound of the formula I wherein $R_1$ is hydrogen, methyl, methyl, —CO—CH$_2$—NH$_2$ or —CO—CH(CH$_3$)—NH$_2$, and $R_3$ is amino, —NH—CO—$R_6$ or —NH—A—$R_7$, where $R_6$, $R_7$ and A have the meanings previously defined, by catalytic hydrogenation or a compound of the formula

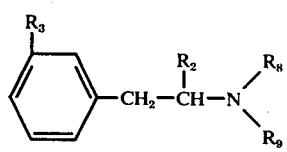 (XII)

wherein
$R_2$ and $R_3$ have the same meanings as in formula I,
$R_8$ is hydrogen or a protective substituent which can be removed by hydrogenation, such as benzyl or carbobenzoxy, and
$R_9$ is hydrogen, methyl, ethyl, —CO—CH$_2$—NH—$R_{10}$ or —CO—CH(CH$_3$)—NH—$R_{10}$, where $R_{10}$ is a protective substituent which can be removed by hydrogenation, provided, however, that at least one of $R_8$ and $R_{10}$ is a protective substituent which can be removed by hydrogenation, with hydrogen in the presence of a hydrogenation catalyst, such as platinum, palladium or Raney nickel.

If $R_3$ in a starting compound of the formula XII is nitro, this substituent is simultaneously reduced to amino by the catalytic hydrogenation.

The starting compounds of the formula XII are known compounds or may be prepared by known methods.

Method F

For the preparation of a compound of the formula I wherein $R_1$ is hydrogen, methyl or ethyl, by hydrolizing a compound of the formula

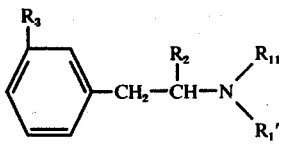

(XIII)

wherein $R_2$ and $R_3$ have the same meanings as in formula I, $R_1'$ is hydrogen, methyl or ethyl, and $R_{11}$ is a protective substituent which is removable by hydrolysis, preferably acyl, such as formyl, acetyl or benzoyl, which is more easily split off under hydrolysis conditions in comparison to similarly removable substituents which may be present in $R_3$.

The starting compounds of the formula XIII may be prepared by conventional methods, for instance by corresponding N-substitution of a compound of the formula II, or from precursors of compounds of the formula II.

Method G

For the preparation of a compound of the formula I wherein $R_3$ is amino, by either hydrogenating or hydrolizing a compound of the formula

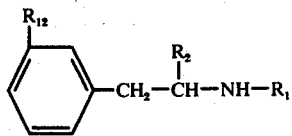

(XIV)

wherein $R_1$ and $R_2$ have the meanings defined in formula I, and $R_{12}$ is nitro or $-NH-R_{13}$, where $R_{13}$ is a protective substituent which can be removed by hydrogenation or hydrolysis.

When $R_{12}$ in starting compound XIV is nitro or $-NHR_{13}$, where $R_{13}$ is a protective substituent removable by hydrogenation, such as benzyl or carbobenzoxy, the starting compound is hydrogenated with hydrogen in the presence of a hydrogenation catalyst, such as platinum, palladium or Raney nickel.

When $R_{12}$ in starting compound XIV is $-NHR_{13}$, where $R_{13}$ is a protective group removable by hydrolysis, such as acyl, the starting compound is hydrolized under acid or basic conditions, but the protective group $R_{13}$ must be more readily removable by hydrolysis, especially with aqueous acids or bases, than any embodiment of $R_1$ which will also split off when subjected to hydrolysis with conventional hydrolyizing agents.

The starting compounds of the formula XIV may be prepared by conventional methods, for example, by subjecting a compound of the formula

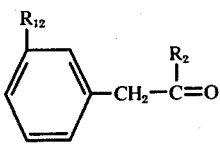

(XV)

wherein $R_2$ has the same meanings as in formula I, and $R_{12}$ has the same meaning as in formula XIV, to reductive amination with an amine of the formula $NH_2R_1$.

Those compounds of the formula I wherein $R_2$ is methyl exist in the form of racemates or optically active isomers. The pure optical isomers may be obtained by using starting compounds of corresponding configuration in methods A and C to G. These optically active starting compounds may be obtained by conventional methods.

The optically active isomers may also be obtained by separating the racemate obtained as an end product by any of the above-described methods into its optically active components by conventional separation procedures.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, acetic acid, propionic acid, citric acid, oxalic acid, maleic acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-(3'-Formylamino-phenyl)-2-amino-propane hydrochloride by method A 1-(m-Nitro-phenyl)-2-nitro-propane (m. p. 56°–58° C.) was prepared by refluxing m-nitro-benzaldehyde and nitroethane in toluene in the presence of benzoic acid and piperidine for 5 hours. The product was then hydrogenated, first in the presence of palladized charcoal in pyridine at 5 atmospheres and room temperature and then in the presence of Raney nickel and ammonia in methanol at 5 atmospheres and 40° C., to form 1-(m-amino-phenyl)-2-amino-propane (b.p. 120°–141° C. at 0.1 mm Hg; m.p. 78°–79° C.).

3 gm of this base and 2.32 gm of maleic acid were dissolved in hot acetonitrile, and upon cooling of the solution 1-(3'-amino-phenyl)-2-amino-propane maleate, m.p. 131°–132° C. (from acetonitrile), crystallized out.

255 gm of 1-(3'-amino-phenyl)-2-amino-propane were dissolved in methanol, and the solution was acidified with ethereal hydrochloric acid. The monohydrochloride thus obtained was refluxed for 2 hours in 225 ml of formic acid, and the reaction mixture was then evaporated in a water aspirator vacuum, leaving a yellow oil which solidified upon being digested with ether. The solidified product was recrystallized from ethanol by addition of ether, yielding the compound of the formula

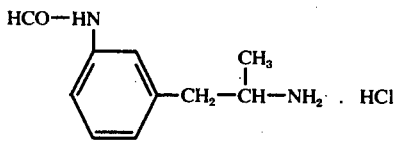

which had a melting point of 150°–153° C.

EXAMPLE 2

1-(3'-Acetamino-phenyl)-2-amino-propane hydrochloride by method A 15 gm of 1-(3'-amino-phenyl)-2-amino-propane were dissolved in glacial acetic acid, and ethereal hydrochloric acid was added to the solution. The resulting solution of 1-(3'-amino-phenyl)-2-amino-propane monohydrochloride was admixed with 15 ml of acetic acid anhydride, and the mixture was stirred for 10 minutes at room temperature. Thereafter, the reaction mixture was evaporated in a water aspirator vacuum, whereupon 1-(3'-acetamino-phenyl)-2-amino-propane hydrochloride crystallized out. Recrystallized from ethanol, the product had a melting point of 181°–183° C.

EXAMPLE 3

Using a procedure analogous to that described in Example 2, 1-(3'-acetamino-phenyl)-2-methylamino-propane hydrochloride, m.p. 162°–165° C., was obtained from 1-(3'-amino-phenyl)-2-methylamino-propane hydrochloride and acetic acid anhydride.

EXAMPLE 4

Using a procedure analogous to that described in Example 2, 1-(3'-acetamino-phenyl)-2-ethylamino-ethane hydrochloride, m.p. 180°–182° C., of the formula

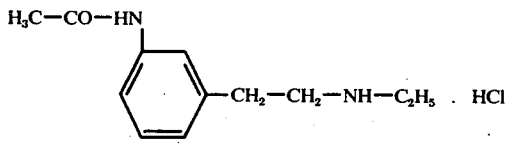

was obtained from 1-(3'-amino-phenyl)-2-ethylamino-ethane hydrochloride and acetic acid anhydride.

EXAMPLE 5

1-[3'-(Dimethylamino-sulfonyl-amino)-phenyl]-2-amino-propane and its maleate by method B m-Nitro-benzyl alcohol was prepared by subjecting m-nitro-benzaldehyde to the Cannizarro Reaction at 45° C., with an aqueous formalin solution and potassium hydroxide. The m-nitro-benzyl alcohol was reacted with thionyl chloride to form m-nitro-benzyl chloride (m.p. 45° C.). By refluxing m-nitro-benzyl chloride with sodium cyanide in aqueous-ethanolic solution for five hours in the presence of potassium iodide, m-nitro-benzyl cyanide (m.p. 58° C.) was prepared which was subsequently hydrolized by boiling with concentrated hydrochloric acid to form m-nitrophenyl-acetic acid. The m-nitrophenyl-acetic acid thus obtained was then converted into 1-(m-nitrophenyl)-propanone-(2), m.p. 62° C., by the method of Shtacker et al, J. Med. Chem. 15, 1174 (1972), and the 1-(m-nitro-phenyl)-propanone-(2) was reduced in water with nascent hydrogen generated by iron powder and concentrated hydrochloric acid, followed by 3 hours' stirring. The reduction product, 1-(m-amino-phenyl)-propanone-(2), was recovered from the reaction mixture by extraction with ether. Since the product thus obtained was not distillable without decomposition, it was purified via its oxalate, m.p. 127°–129° C., which was prepared by dissolving the base in acetonitrile and adding oxalic acid to the solution. By adding aqueous sodium hydroxide to the oxalate and extracting the aqueous mixture with ether, the free base was again obtained.

13.3 gm of dimethylamino-sulfochloride was added dropwise to a solution of 11.5 gm of 1-(3'-amino-phenyl)-propanone-(2) in 57 ml of pyridine at 10°–20° C., and the resulting mixture was stirred for several hours at room temperature. Thereafter, it was poured into ice water, the aqueous mixture was acidified with concentrated hydrochloric acid and extracted with ether, and the ether extract was evaporated, leaving 13.5 gm of 1-[3'-(dimethylamino-sulfonyl-amino)-phenyl]-propanone-(2). This compound was hydrogenated in methanol in the presence of Raney nickel and ammonia at 5 atmospheres and 60° C., whereupon the catalyst was separated by suction filtration, and the filtrate was evaporated, leaving as a residue 1-[3'-(dimethylamino-sulfonyl-amino)-phenyl]-2-amino-propane. The residue was dissolved in acetonitrile, the solution was acidified with maleic acid, the precipitate formed thereby was collected by suction filtration and recrystallized from acetonitrile, yielding the maleate of the formula

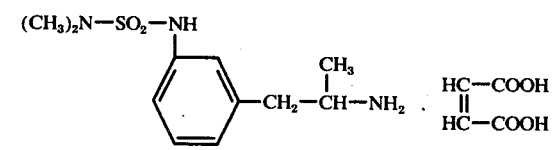

which had a melting point of 128°–131° C.

EXAMPLE 6

1-[3'-(Ethoxycarbonyl-amino)-phenyl]-2-amino-propane and its hydrochloride by method D 12 gm of ethyl chloroformate were added dropwise to a solution of 23.9 gm of 1-(3'-amino-phenyl)-propanone-(2) oxalate in 150 ml of pyridine at 10°–20° C., and the resulting mixture was first stirred for 6 hours at room temperature and then allowed to stand at room temperature for several hours. Thereafter, the reaction mixture was diluted with ice water, acidified with concentrated hydrochloric acid and extracted with chloroform. The organic extract solution was evaporated, and the residue was distilled in vacuo, yielding 14.5 gm of 1-[3'-ethoxycarbonyl-amino)-phenyl]-propanone-(2), b.p. 170°–173° C. at 0.01 mm Hg. This ketone was hydrogenated in methanol in the presence of Raney nickel and ammonia at 5 atmospheres and 70°–80° C. to form 1-[3'-(ethoxycarbonyl-amino)-phenyl]-2-amino-propane. After filtering off the catalyst and evaporating the filtrate, the residue was dissolved in acetonitrile, the solution was acidified with ethereal hydrochloric acid, and the precipitate formed thereby was collected and recrystallized from acetonitrile by addition of a little water, yielding the hydrochloride of the formula

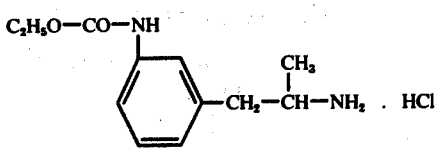

which had a melting point of 185°–186° C.

EXAMPLE 7

1-(3′-Ureido-phenyl)-2-amino-propane and its maleate by method D 15 gm of 1-(3′-amino-phenyl)-propanone-(2) were dissolved at 35° C. in a mixture of 24 ml of glacial acetic acid and 48 ml of water, and then a solution of 8.1 gm of potassium cyanate in 45 ml of water was added dropwise at 35° C., while stirring. The resulting mixture was stirred for 2 hours at room temperature and was then allowed to stand overnight. Thereafter, the reaction mixture was diluted with water and extracted with chloroform, the organic extract was evaporated, and the residue was recrystallized from ethyl acetate, yielding 10 gm of 1-(3′-ureido-phenyl)-propanone-(2) having a melting point of 123°–124° C.

This ketone was converted into 1-(3′-ureidophenyl)-2-amino-propane by catalytic hydrogenation in the presence of ammonia analogous to Example 6, and the hydrogenation product was purified by chromatography on a silicagel column, using first methanol/chloroform (2:8) and then methanol/glacial acetic acid (49:1) as the flow agent. The methanolic eluate was evaporated, the residue was admixed with sodium hydroxide and ethyl acetate, and the free base liberated thereby was dissolved in methanol, the solution was acidified with maleic acid, ether was added, and the precipitate formed thereby was recrystallized from ethanol/ethyl acetate, yielding the maleate of the formula

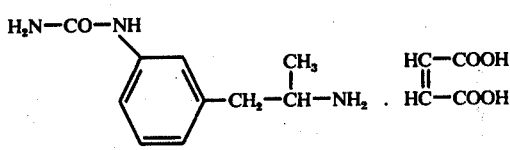

which had a melting point of 139°–141° C.

EXAMPLE 8

1-[3′-(Methoxycarbonyl-amino)-phenyl]-2-amino-propane and its hydrochloride by method D 1-[3′-(methoxycarbonyl-amino)-phenyl]-propanone-(2), m.p. 93°–95° C. (reprecipitated from isopropanol with petroleum ether), was prepared in analogy to Example 6. The ketone was then hydrogenated in methanol in the presence of ammonia and Raney nickel at 60° C. and 5 atmospheres to form 1-[3′-(methoxycarbonyl-amino)-phenyl]-2-amino-propane. After separating the catalyst by suction filtration and evaporating the methanol from the filtrate in a water aspirator vacuum, the residue was dissolved in acetonitrile, and the solution was acidified with ethereal hydrochloric acid. The precipitate formed thereby was collected and recrystallized from acetonitrile, yielding the hydrochloride of 1-[3′-(methoxycarbonyl-amino)-phenyl]-2-amino-propane, m.p. 185°–187° C.

EXAMPLE 9

1-]3′-(N′-Methyl-ureido)-phenyl]-2-amino-propane and its maleate by method D 2.85 gm of methylisocyanate were added dropwise to a solution of 7.5 gm of 1-(3′-amino-phenyl)-propanone-(2) in 100 ml of acetonitrile at room temperature. The resulting mixtures was stirred for 4 hours at 20°–25° C. while cooling on an ice bath, if necessary, and then the acetonitrile was distilled off at 20°–25° C. in vacuo. The residue was recrystallized from ethyl acetate by addition of petroleum ether, and the crystals were collected by suction filtration and washed with ether, yielding 5.7 gm of 1-[3′-(N′-methylureido)-phenyl]-propanone-(2) having a melting point of 77°–82° C.

The ketone thus obtained was catalytically hydrogenated in the presence of ammonia in analogy to Example 6, and the hydrogenation product was purified by column-chromatography in analogy to Example 7. The free base was liberated from the residue of the evaporated methanol/glacial acetic acid eluate by addition of sodium hydroxide and methylene chloride. The base was dissolved in methanol, the solution was acidified in the maleic acid, and ether was added, yielding the maleate of the formula

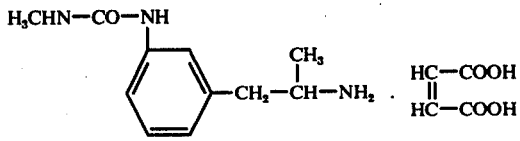

which had a melting point of 128°–131° C.

EXAMPLE 10

1-[3′-(Ethylthiocarbonyl-amino)-phenyl]-2-amino-propane and its hydrochloride by method F A mixture of 1-(3′-amino-phenyl)-2-amino-propane and 12.5 ml of ethyl formate was boiled for 10 hours, and then the reaction mixture was evaporated, leaving 1-(3′-aminophenyl)-2-(formyl-amino)-propane. 4.45 gm of this amide were dissolved in 25 ml of pyridine, 2.6 ml of chlorothioformic acid-S-ethyl ester were added to the solution at 10°–20° C., and the mixture was allowed to stand for a few hours. Thereafter, the reaction solution was poured into ice water, and the aqueous mixture was extracted with ether. The ethereal extract was washed five times with water and once briefly with 1/10 N hydrochloric acid, and was then evaporated, leaving as a residue 1-[3′-(ethylthiocarbonyl-amino)-phenyl]-2-(formyl-amino)-propane. The residue was added to a mixture of 75 ml of methanol and 5 ml of concentrated hydrochloric acid, and the mixture was allowed to stand for three days at room temperature. Thereafter, the resulting solution was evaporated, the residue was triturated with acetonitrile, and the crystalline product formed thereby was recrystallized from acetonitrile and a little water, yielding the hydrochloride of the formula

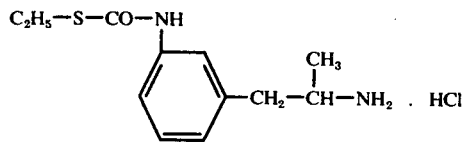

which had a melting point of 185°–186° C.

EXAMPLE 11

1-(3'-Ureido-phenyl)-2-methylamino-propane, its oxalate and its maleate 7 gm of 1-(3'-ureido-phenyl)-propanone-(2) were hydrogenated in 70 ml of methanol with 8.5 ml of methylamine in the presence of Raney nickel at 60° C and 5 atmospheres to form 1-(3'-ureido-phenyl)-2-methylamino-propane. Thereafter, the catalyst was removed by filtration, the methanol was evaporated from the filtrate, the residue was dissolved in methanol, and the solution was acidified with oxalic acid, yielding the oxalate of 1-(3'-ureido-phenyl)-2-methylamino-propane. The oxalate was dissolved in water, the solution was extracted with chloroform, the organic extract was admixed with sodium hydroxide, and the free base liberated thereby was extracted with m-butanol. The butanolic extract was evaporated, the residue was dissolved in ethanol, and the calculated amount of maleic acid was added to the ethanolic solution. The precipitate formed thereby was collected by suction-filtration and dried, yielding the maleate of the formula

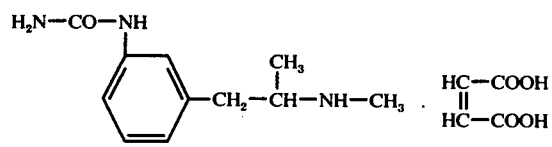

which had a melting point of 152°–153° C.

EXAMPLE 12

1-(3'-Ureido-phenyl)-2-amino-propane and its maleate

A solution of 22.5 gm of hydroxylamine hydrochloride in 69 ml of water was added to a solution of 48 gm of 1-(3'-ureido-phenyl)-propanone-(2), and then a solution of 34.5 gm of sodium carbonate in 87.5 ml of water was added dropwise at 50°–60° C. The resulting mixture was boiled for 1 hour and then diluted with water, whereupon 1-(3'-ureido-phenyl)-propanone-(2)-oxime (m.p. 152°–155° C) crystallized out. The oxime was collected by suction filtration and hydrogenated in methanol in the presence of Raney nickel at 60° C and 5 atmospheres to form 1-(3'-ureido-phenyl)-2-amino-propane. After the catalyst had been removed by filtration and the solvent was evaporated from the filtrate, the hydrogenation product was purified by chromatography on a silicagel column, using methanol/glacial acetic acid (49:1) as the flow agent. The eluate was evaporated, leaving as the residue the acetate of 1-(3'-ureido-phenyl)-2-amino-propane, from which the free base was liberated with sodium hydroxide. The base was extracted with n-butanol, the extract was evaporated, the residue was dissolved in ethanol, the solution was acidifed with maleic acid, and the maleate of 1-(3'-ureido-phenyl)-2-amino-propane, m.p. 139°–141° C, was precipitated by addition of ethyl acetate.

EXAMPLE 13

1-(3'-Nitro-phenyl)-2-amino-propane and its hydrochloride

A mixture consisting of 35.8 gm of 1-(3'-nitro-phenyl)-propanone-(2), 32 ml of formamide and 10.2 ml of 98–100% formic acid was heated at 170° C while continuously distilling off the water formed by the reaction. The evolution of carbon dioxide ceases after one hour of heating, at which time the reaction mixture was cooled and then poured into ice water. The crystalline precipitate formed thereby was collected by suction filtration and reprecipitated from ethyl acetate and petroleum ether, yielding 1-(3'-nitro-phenyl)-2-(formyl-amino)-propane, m.p. 99°–100° C. 34.5 gm of this compound were refluxed for three hours in 200 ml of concentrated hydrochloric acid. Thereafter, the reaction solution was cooled, diluted with water and extracted with methylene chloride, and the aqueous phase was made strongly alkaline with sodium hydroxide and then extracted with methylene chloride. The organic extract was evaporated, the residue was dissolved in acetonitrile, the solution was acidified with ethereal hydrochloric acid, and the precipitate formed thereby was collected and recrystallized from acetonitrile, yielding the hydrochloride of the formula

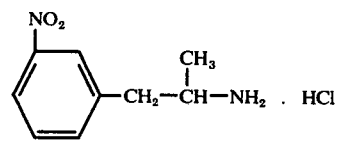

which had a melting point of 171–172° C.

EXAMPLE 14

1-(3'-Ureido-phenyl)-2-(amino-acetamido)-propane hydrochloride

A mixture of 6.755 gm of 1-(3'-ureido-phenyl)-2-amino-propane, 7.315 gm of carbobenzoxy-glycine, 4.41 gm of diisopropylcarbodiimide and 70 ml of benzene was refluxed for two hours. Thereafter, the solvent was evaporated, and the residue was purified by chromatography on a silicagel column, using methanol/chloroform (2:8) as the flow agent. The eluate was evaporated, and the residue was recrystallized from ethyl acetate, yielding 9.5 gm of 1-(3'-ureido-phenyl)- 2-(carbobenzoxyamidoacetyl-amino)-propane, m.p. 125°–135° C, which was then hydrogenated in 100 ml of glacial acetic acid in the presence of 1 gm of palladized charcoal (5%) at 50° C and 5 atmospheres. For the preparation of the hydrochloride, 3.1 gm of benzyl chloride and 50 ml of water were added, and the mixture was hydrogenated at 5 atmospheres until the absorption of hydrogen had ceased. Thereafter, the catalyst was filtered off, the solvent was evaporated from the filtrate, and the residue was crystallized with acetonitrile and recrystallized from methanol, yielding the compound of the formula

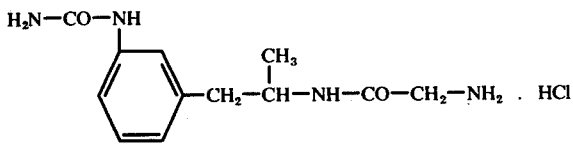

which had a melting point of 212°–215° C.

EXAMPLE 15

1-(3′-Ureido-phenyl)-2-formylamino-propane

A mixture consisting of 4.8 gm of 1-(3′-ureido-phenyl)-2-amino-propane and 5 ml of ethyl formate was refluxed for 5 hours. Thereafter, the reaction solution was evaporated, and the residue was purified by chromatography on a silicagel column, using methanol/chloroform (2:8) as the flow agent. The eluate was evaporated, and the residue was recrystallized from ethanol and ether, yielding the compound of the formula

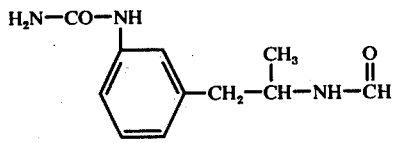

which had a melting point of 133–136° C.

EXAMPLE 16

1-(3′-Ureido-phenyl)-2-(cyanomethyl-amino)-propane and its maleate

A mixture consisting of 4.8 gm of 1-(3′-ureido-phenyl)-2-amino-propane, 3.5 gm of potassium carbonate, 1.6 ml of chloroacetonitrile and 50 ml of acetonitrile was refluxed for two hours. Thereafter, the inorganic precipitate which had formed was separated by suction filtration, the solvent was evaporated from the filtrate, and the residue was purified by chromatography on a silicagel column, using methanol/chloroform (2:8) as the flow agent. The eluate was evaporated, and the residue, 1-(3′-ureido-phenyl)-2-(cyanomethyl-amino)-propane, was dissolved in acetonitrile and the calculated amount of maleic acid was added to the solution. The precipitate formed thereby was collected and recrystallized from acetonitrile, yielding the maleate of the formula

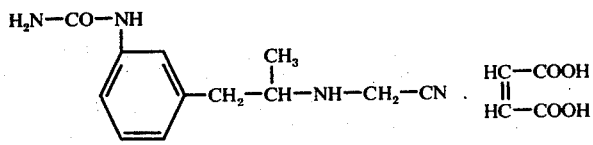

which had a melting point of 129°–131° C (decomp.).

EXAMPLE 17

1-(3′-Amino-phenyl)-2-(phenacyl-amino)-propane dihydrochloride

A mixture consisting of 9.6 gm of 1-(3′-acetamino-phenyl)-2-amino-propane (see Example 2), 10 gm of α-bromoacetophenone, 7 gm of potassium carbonate and 200 ml of acetonitrile was refluxed for 3 hours. Thereafter, the inorganic precipitate which had formed was removed by suction filtration, and 5 gm of oxalic acid were added to the filtrate. The precipitate formed thereby was collected by suction filtration, yielding 6 gm of 1-(3′-acetamino-phenyl)-2-(phenacyl-amino)-propane oxalate, m.p. 136°–140° C. The oxalate was added to 60 ml of ethanolic 10% hydrochloric acid, and the mixture was refluxed for four hours. Thereafter, the reaction solution was evaporated, the residue was caused to crystallize by treating it with acetonitrile and a little water, and the crystallizate was purified by dissolving it in a little water, filtering the solution through activated charcoal, and adding acetonitrile to the filtrate. The dihydrochloride of the formula

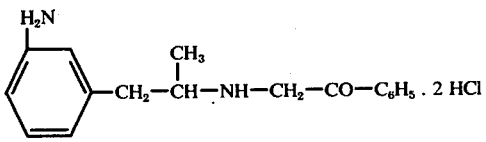

having a melting point of 169°–173° C (decomp.) was obtained.

EXAMPLE 18

1-(3′-Amino-phenyl)-2-(benzylaminoacetyl-amino)-propane dihydrochloride 7.5 gm of chloroacetyl chloride were added dropwise to a mixture of 18 gm of 1-(3′-nitro-phenyl)-2-amino-propane, 14 gm of potassium carbonate and 150 ml of acetonitrile, whereby the temperature of the mixture rose to 45° C, and the resulting mixture was refluxed for two hours. Thereafter, the reaction mixture was allowed to cool, and then it was diluted with ice water, whereupon 1-(3′-nitro-phenyl)-2-(chloroacetyl-amino)-propane (m.p. 118°–120° C, recrystallized from ethyl acetate/petroleum ether) crystallized out. 17 gm of this compound were added to a mixture of 14 gm of benzylamine and 200 ml of acetonitrile, and the mixture was refluxed for two hours. Thereafter, the benzylamine hydrochloride which had precipitated out was removed by suction filtration, and the filtrate was acidified with ethereal hydrochloric acid, and the crystalline precipitate formed thereby was recrystallized from 1 N hydrochloric acid, yielding 11.5 gm of 1-(3′-nitro-phenyl)-2-(benzylaminoacetyl-amino)-propane hydrochloride, m.p. 167°–170° C. This hydrochloride was hydrogenated in methanol in the presence of Raney nickel at atmospheric pressure and room temperature, yielding 1-(3′-aminophenyl)-2-(benzylaminoacetyl-amino)-propane hydrochloride which was dissolved in ethanol, and the solution was admixed with the calculated amount of ethereal hydrochloric acid, yielding the dihydrochloride of the formula

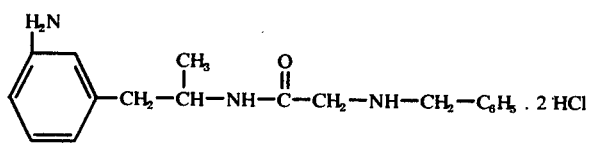

which had a melting point of 234°–236° C (decomp.).

EXAMPLE 19

1-(3'-Amino-phenyl)-2-(aminoacetyl-amino)-propane hydrochloride 6 gm of the dihydrochloride obtained in the preceding example were de-benzylated by hydrogenation in 60 ml of methanol in the presence of 0.5 gm of palladized charcoal at 60° C and 5 atmospheres. Thereafter, the catalyst was removed by filtration, the solvent was evaporated from the filtrate, and the residue was recrystallized from ethanol and acetonitrile, yielding 1-(3'-amino-phenyl)-2-(aminoacetyl-amino)-propane hydrochloride, m.p. 195°–197° C.

EXAMPLE 20

1-(3'-Amino-phenyl)-2-(methoxycarbonyl-amino)-propane and its maleate 5.33 ml of methyl chloroformate were added dropwise to a mixture consisting of 12.6 gm of 1-(3'-nitro-phenyl)-2-amino-propane, 9.8 gm of potassium carbonate and 100 ml of acetonitrile, whereby the temperature of the mixture rose to 45° C, and the resulting mixture was boiled for 2 hours. Thereafter, the reaction mixture was diluted with ice water, and the crystals precipitated thereby were collected by suction filtration, washed with water and dried, yielding 11 gm of 1-(3'-nitro-phenyl)-2-(methoxycarbonyl-amino)-propane, m. p. 104°–105° C. This compound was hydrogenated in methanol in the presence of Raney nickel at atmospheric pressure and room temperature. Thereafter, the catalyst was removed by suction filtration, the methanol was distilled out of the filtrate, and the residue, 1-(3'-amino-phenyl)-2-(methoxycarbonyl-amino)-propane, was dissolved in acetonitrile. The resulting solution was admixed with the calculated amount of maleic acid, and the precipitate formed thereby was recrystallized twice from acetonitrile, yielding 5.5 gm of the maleate of the formula

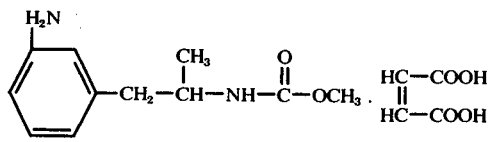

which had a melting point of 125°–127° C.

EXAMPLE 21

1-(3'-Amino-phenyl)-2-formylamino-propane 5.2 gm of 1-(3'-nitro-phenyl)-2-formylamino-propane was hydrogenated in methanol in the presence of Raney nickel at atmospheric pressure and room temperature. Thereafter, the catalyst was filtered off, the solvent was evaporated from the filtrate, and the residue was chromatographed on a silicagel column, using methanol/chloroform (2:8) as the flow agent. The eluate was evaporated, and the residue was recrystallized from ethyl acetate, yielding 1-(3'-aminophenyl)-2-formylamino-propane which had a melting point of 107°–108° C.

The compounds of the present invention, that is, those embraced by formula I above and their non-toxic, pharmacologically acceptable acid addition salts, have useful properties. More particularly, they exhibit very effective and long-lasting sympathomimetic and CNS-stimulating activities in warm-blooded animals, such as cats, dogs, rats, mice; they especially produce a long-lasting hypertensive effect. Therefore, the compounds of this invention are useful as circulation enhancers.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective hypertensive dosage unit of the compounds according to the present invention is from 0.016 to 3.4 mgm/kg body weight, preferably 0.083 to 1.67 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 22

Tablets

The tablet composition is compounded from the following ingredients:

| | |
|---|---|
| 1-(3'-Formylamino-phenyl)-2-amino-propane hydrochloride | 5 parts |
| Stearic acid | 6 " |
| Dextrose | 589 " |
| Total | 600 parts |

Preparation

The ingredients are intimately admixed with each other, and the mixture is compressed in conventional manner into 600 mgm-tablets. Each tablet contains 5 mgm of the phenylakylamine and is an oral dosage unit composition with effective hypertensive action.

EXAMPLE 23

Suppositories

The suppository composition is compounded from the following ingredients:

| | |
|---|---|
| 1-(3'-Ureido-phenyl)-2-(amino-acetyl-amino)-propane hydrochloride | 50 parts |

-continued

| | | |
|---|---:|---|
| Lactose, powdered | 50 | " |
| Suppository base (e.g. cocoa butter) | 1600 | " |
| Total | 1700 parts | |

Preparation

The lactose is intimately admixed with the phenylalkylamine, and the mixture is homogeneously blended into the molten suppository base. 1700 mgm-portions of the resulting composition are poured into cooled suppository molds and allowed to harden therein. Each suppository contains 50 mgm of the phenylakylamine and is a rectal dosage unit composition with effective hypertensive action.

Analogous results are obtained when any one of the other phenylalkylamines embraced by formula I or a non-toxic, pharmacologically acceptable acid addition salt thereof is substituted for the particular phenylakylamine in Examples 22 and 23. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

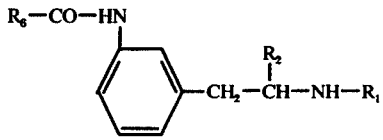

wherein
$R_1$ is hydrogen or $-(CH_2)_n-H$, where $n$ is 1 or 2,
$R_2$ is hydrogen or methyl, and
$R_6$ is hydrogen or methyl, or a non-toxic, pharmacologically acceptable acid addition salt thereof.

2. A compound of claim 1,
where
$R_1$ is hydrogen,
$R_2$ is hydrogen or methyl, and
$R_6$ is hydrogen.

3. A compound of claim 2, which is 1-(3'-formylamino-phenyl)-2-amino-propane or a non-toxic, pharmacologically acceptable acid addition salt thereof.

4. A hypertensive pharmaceutical dosage unit composition consisting essentially of an inert pharmaceutical carrier and an effective hypertensive amount of a compound of claim 1.

5. The method of raising the blood pressure in a warm-blooded animal in need of such treatment, which comprises administering to said animal an effective hypertensive amount of a compound of claim 1.

* * * * *

UNITED STATES PATENT OFFICE
CERTIFICATE OF CORRECTION

Patent No. 4,015,011                    Dated March 29, 1977

Inventor(s) Kurt Schromm et al.

It is certified that error appears in the above-identified patent and that said Letters Patent are hereby corrected as shown below:

Column 1, Line 42 - "for" should read "of"

" 3, " 22 - "or" should read "of"

" 4, " 40 - "methyl"(second occurrence) should read "ethyl"

" 4, " 44 - "or" should read "of"

" 9, " 15 - "method D" should read "method B"

" 11, " 27 - "m-butanol." should read "n-butanol".

Signed and Sealed this

Seventh Day of June 1977

[SEAL]

Attest:

RUTH C. MASON  
*Attesting Officer*

C. MARSHALL DANN  
*Commissioner of Patents and Trademarks*